US012673217B2

(12) United States Patent
Sowards et al.

(10) Patent No.: US 12,673,217 B2
(45) Date of Patent: Jul. 7, 2026

(54) SHAPE-SENSING SYSTEMS WITH VIBRATION-ASSISTED TORSION MANAGEMENT AND METHODS THEREOF

(71) Applicant: Bard Access Systems, Inc., Salt Lake City, UT (US)

(72) Inventors: Steffan Sowards, Salt Lake City, UT (US); William Robert McLaughlin, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 278 days.

(21) Appl. No.: 18/233,782

(22) Filed: Aug. 14, 2023

(65) Prior Publication Data

US 2024/0050768 A1 Feb. 15, 2024

Related U.S. Application Data

(60) Provisional application No. 63/398,160, filed on Aug. 15, 2022.

(51) Int. Cl.
*A61N 5/067* (2006.01)

(52) U.S. Cl.
CPC .................................... *A61N 5/067* (2021.08)

(58) Field of Classification Search
CPC .... A61N 5/067; A61B 5/065; A61B 5/02007; A61B 2017/00203; A61B 2034/2061;
(Continued)

(56) References Cited

U.S. PATENT DOCUMENTS

2009/0208143 A1* 8/2009 Yoon ................... A61B 5/0062
                                                          382/312
2015/0031987 A1* 1/2015 Pameijer .............. A61B 5/0084
                                                          600/424
(Continued)

FOREIGN PATENT DOCUMENTS

WO         2021168061 A1     8/2021

OTHER PUBLICATIONS

PCT/US2023/030165 filed Aug. 14, 2023 International Search Report and Written Opinion dated Nov. 23, 2023.

*Primary Examiner* — Rex R Holmes
(74) *Attorney, Agent, or Firm* — Rutan & Tucker LLP

(57) ABSTRACT

A shape-sensing system can include an optical-fiber probe and a vibration-assisted torsion-management means for managing torsion in the optical-fiber probe. The optical-fiber probe can be configured to be removably disposed in an elongate medical device. The optical-fiber probe can include an inner construction and an outer construction over the inner construction but detached therefrom over a majority of the optical-fiber probe. The inner construction can include one or more optical-fiber cores disposed in a cladding. The outer construction can include a mechanical layer. The vibration-assisted torsion-management means can be operably coupled to the optical-fiber probe for vibrating either the inner construction or the outer construction of the optical-fiber probe relative to the other, which mitigates or eliminates any optical signal-distorting torsion in the inner construction of the optical-fiber probe. A method of the shape-sensing system can include managing torsion of the optical-fiber probe with the vibration-assisted torsion-management means.

20 Claims, 7 Drawing Sheets

(58) Field of Classification Search
    CPC ..... A61B 5/0051; A61B 5/103; A61B 5/6852;
        A61B 34/20; A61B 5/0084; A61B 90/00;
        G01B 11/18; G01B 11/24; G01D 5/35377
    See application file for complete search history.

(56)                    References Cited

U.S. PATENT DOCUMENTS

2021/0239911 A1 *   8/2021   Song .................... A61B 5/0084
2021/0267696 A1     9/2021   Degertekin et al.

* cited by examiner

SHAPE-SENSING SYSTEMS WITH VIBRATION-ASSISTED TORSION MANAGEMENT AND METHODS THEREOF

PRIORITY

This application claims the benefit of priority to U.S. Provisional Patent Application No. 63/398,160, filed Aug. 15, 2022, which is incorporated by reference in its entirety into this application.

BACKGROUND

Shape-sensing systems are susceptible to torsion-related distortion in the optical-fiber probes thereof, which can lead to inaccurate shape-sensing, medical decisions based thereon, and reduced patient outcomes as a result.

Disclosed herein are shape-sensing systems with vibration-assisted torsion management and methods thereof that address the foregoing.

SUMMARY

Disclosed herein is a shape-sensing system including, in some embodiments, an optical-fiber probe and a vibration-assisted torsion-management means for managing torsion in the optical-fiber probe. The optical-fiber probe is configured to be removably disposed in an elongate medical device. The optical-fiber probe includes an inner construction and an outer construction over the inner construction but detached therefrom over a majority of the optical-fiber probe. The inner construction includes one or more optical-fiber cores disposed in a cladding. The outer construction includes a mechanical layer. The vibration-assisted torsion-management means is operably coupled to the optical-fiber probe for vibrating either the inner construction or the outer construction of the optical-fiber probe relative to the other, which mitigates or eliminates any optical signal-distorting torsion in the inner construction of the optical-fiber probe.

In some embodiments, the mechanical layer is metal tubing.

In some embodiments, the metal tubing is configured to convey electrical signals along a length of the optical-fiber probe.

In some embodiments, the mechanical layer is polymer tubing.

In some embodiments, the mechanical layer includes one or more metal wires disposed in the polymer tubing.

In some embodiments, the one-or-more metal wires are configured to convey electrical signals along a length of the optical-fiber probe.

In some embodiments, the vibration-assisted torsion-management means includes a vibration motor or actuator operably coupled to the optical-fiber probe. The vibration motor or actuator is selected from an eccentric rotating-mass vibration motor, a linear resonant actuator, and a solenoid actuator.

In some embodiments, the vibration motor or actuator is disposed in a handle about a proximal portion of the optical-fiber probe.

In some embodiments, the vibration motor or actuator is started by a switch of the handle.

In some embodiments, the vibration motor or actuator is disposed in a probe-side connector about a proximal-end portion of the optical-fiber probe.

In some embodiments, the vibration motor or actuator is started by a switch of the probe-side connector of the optical-fiber probe.

In some embodiments, the vibration motor or actuator is disposed in another component of the shape-sensing system proximal of a probe-side connector about a proximal-end portion of the optical-fiber probe. The vibration motor or actuator in the other component of the shape-sensing system is configured to transfer vibrations to the optical-fiber probe through the probe-side connector of the optical-fiber probe.

In some embodiments, the vibration motor or actuator is started by a switch of the other component of the shape-sensing system, speech-recognition logic in the other component of the shape-sensing system, or torsion-detection logic in the other component of the shape-sensing system.

In some embodiments, each fiber core of the one-or-more fiber cores of the optical-fiber probe include a number of fiber Bragg grating ("FBG") sensors along at least a distal portion of the optical-fiber probe.

In some embodiments, the shape-sensing system further includes an optical interrogator and a console. The optical interrogator is configured to send input optical signals into the optical-fiber probe and receive FBG sensor-reflected optical signals from the optical-fiber probe. The console includes one or more processors, memory, and executable instructions stored in the memory that cause the console to perform a set of operations upon execution of the instructions by the one-or-more processors. The set of operations include receiving the FBG sensor-reflected optical signals from the optical interrogator; converting the FBG sensor-reflected optical signals into converted electrical signals with optical signal-converter logic of the console; and determining, in a real-time determination, at least a shape of the optical-fiber probe from the converted electrical signals with shape-sensing logic of the console.

In some embodiments, the set of operations further includes tracking of the vibrating of the optical-fiber probe by the vibration-assisted torsion-management means with vibration-tracking logic of the console; and removing from the converted electrical signals any portion thereof related to vibration-assisted torsion management for at least the shape of the optical-fiber probe.

Also disclosed herein is a method of a shape-sensing system including an optical signal-sending step, an optical signal-receiving step, an optical probe-vibrating step, an optical signal-converting step, and a shape-determining step. The optical signal-sending step includes sending input optical signals into an optical-fiber probe with an optical interrogator while the optical-fiber probe is advanced through a vasculature of a patient. The optical-fiber probe includes an inner construction and an outer construction over the inner construction but detached therefrom over a majority of the optical-fiber probe. The inner construction includes one or more optical-fiber cores disposed in a cladding. The outer construction includes a mechanical layer. The optical signal-receiving step includes receiving reflected optical signals from the optical-fiber probe with the optical interrogator. The optical probe-vibrating step includes vibrating either the inner construction or the outer construction of the optical-fiber probe relative to the other with a vibration-assisted torsion-management means operably coupled to the optical-fiber probe. The vibration-assisted torsion-management means manages torsion in the optical-fiber probe while the optical-fiber probe is advanced through the vasculature. The optical signal-converting step includes converting the reflected optical signals into converted electrical signals with optical signal-converter logic of a console including the optical interrogator or operably connected thereto. The shape-determining step includes determining, in a real-time determination, at least a shape of the optical-fiber probe from the converted electrical signals with shape-sensing logic of the console.

In some embodiments, the further includes a vibration-tracking step and a vibration signal-removing step. The vibration-tracking step includes tracking the vibrating of the optical-fiber probe by the vibration-assisted torsion-management means with vibration-tracking logic of the console. The vibration signal-removing step includes removing from the converted electrical signals any portion thereof related to vibration-assisted torsion management for at least the shape of the optical-fiber probe.

In some embodiments, the mechanical layer is metal tubing, polymer tubing, or polymer tubing including one or more metal wires disposed in the polymer tubing. The metal tubing or the one-or-more metal wires are configured convey electrical signals over the optical-fiber probe.

In some embodiments, the optical probe-vibrating step includes vibrating the optical-fiber probe with a vibration motor or actuator operably coupled to the optical-fiber probe. The vibration motor or actuator is selected from an eccentric rotating-mass vibration motor, a linear resonant actuator, and a solenoid actuator.

These and other features of the concepts provided herein will become more apparent to those of skill in the art in view of the accompanying drawings and following description, which describe particular embodiments of such concepts in greater detail.

DRAWINGS

DESCRIPTION

Figure 1:
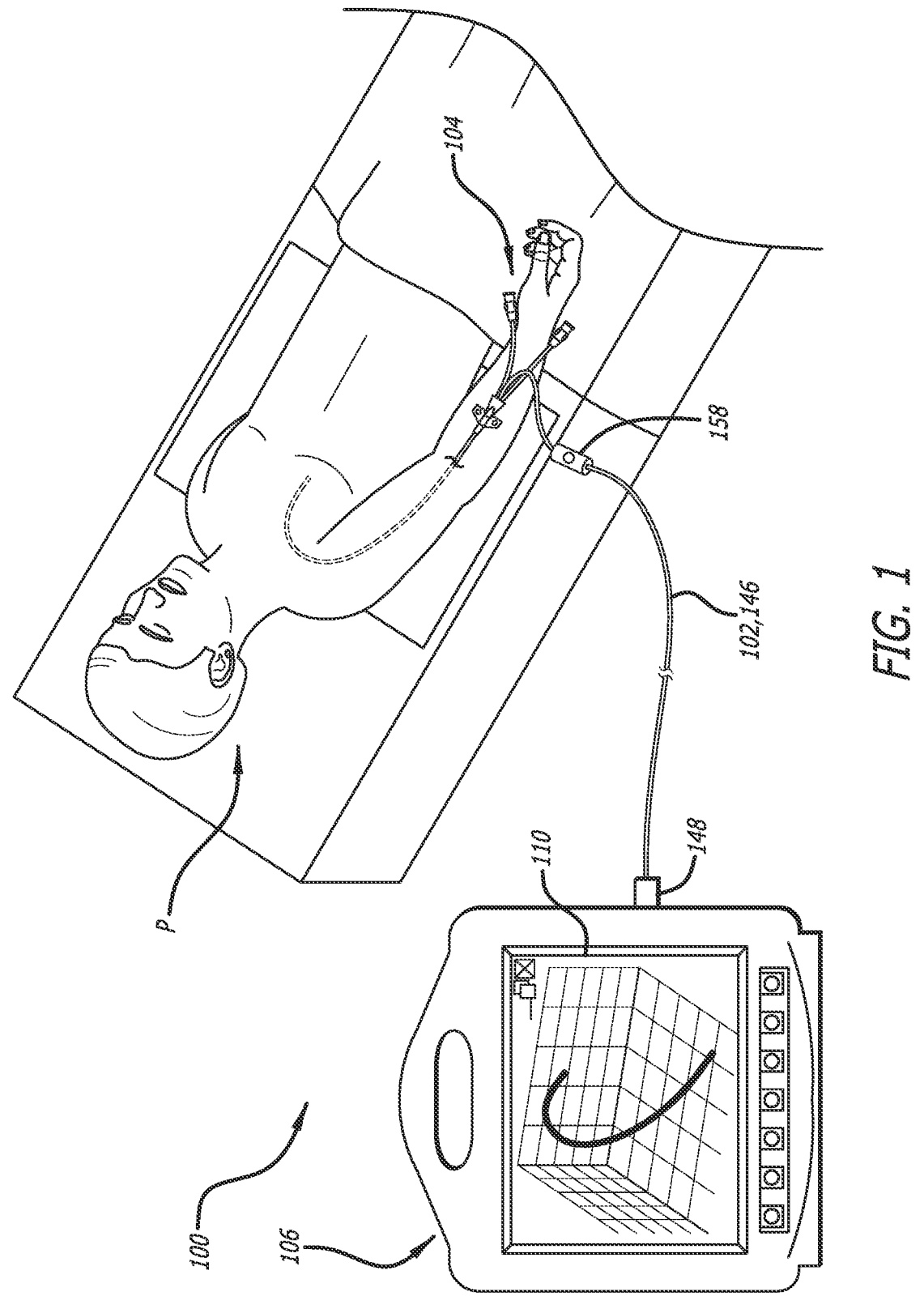
FIG. 1 illustrates a shape-sensing system in use on a patient, the shape-sensing system including vibration-assisted torsion management for an optical-fiber probe in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. In addition, any of the foregoing features or steps can, in turn, further include one or more features or steps unless indicated otherwise. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or "proximal section" of, for example, a medical device includes a portion or section of the medical device intended to be near a clinician when the medical device is used on a patient. Likewise, a "proximal length" of the medical device includes a length of the medical device intended to be near the clinician when the medical device is used on the patient. A "proximal end" of the medical device is an end of the medical device intended to be near the clinician when the medical device is used on the patient. The proximal portion, the proximal section, or the proximal length of the medical device can include the proximal end of the medical device, and, in such instances, the proximal portion, the proximal section, or the proximal length of the medical device can be further specified as a "proximal-end portion," a "proximal-end section," or a "proximal-end length" of the medical device. That said, the proximal portion, the proximal section, or the proximal length of the medical device need not include the proximal end of the medical device. Indeed, unless context suggests otherwise, the proximal portion, the proximal section, or the proximal length of the medical device is not a terminal portion, terminal section, or terminal length of the medical device.

With respect to "distal," a "distal portion" or "distal section" of, for example, a medical device includes a portion or section of the medical device intended to be near or in a patient when the medical device is used on the patient. Likewise, a "distal length" of the medical device includes a length of the medical device intended to be near or in the patient when the medical device is used on the patient. A "distal end" of the medical device is an end of the medical device intended to be near or in the patient when the medical device is used on the patient. The distal portion, the distal section, or the distal length of the medical device can include the distal end of the medical device, and, in such instances, the distal portion, the distal section, or the distal length of the medical device can be further specified as a "distal-end portion," a "distal-end section," or a "distal-end length" of the medical device. That said, the distal portion, the distal section, or the distal length of the medical device need not include the distal end of the medical device. Indeed, unless context suggests otherwise, the distal portion, the distal section, or the distal length of the medical device is not a terminal portion, terminal section, or terminal length of the medical device.

"Logic" can be hardware, firmware, or software configured to perform one or more functions. As hardware, logic can include circuitry having data processing functionality, data storage functionality, or both. An example of such circuitry can include, but is not limited to, a hardware processor (e.g., a microprocessor, one or more processor cores, a digital-signal processor ["DSP" ], a programmable gate array ["PGA" ], a microcontroller, an application-specific integrated circuit ["ASIC" ], etc.) or semiconductor memory. As firmware, the logic can be stored in persistent storage. As software, logic can include one or more processes, instances, Application Programming Interfaces ("APIs"), subroutines, functions, applets, servlets, or routines. Logic can also include source code, object code, a shared library, a dynamic link library ("DLL"), or even one or more instructions. Such software can be stored in any type of suitable non-transitory storage medium or transitory storage medium (e.g., electrical, optical, acoustical, or any other form of propagated signal including carrier waves, infrared signals, or digital signals). An example of a non-transitory storage medium can include, but is not limited to, a programmable circuit; non-persistent storage such as volatile memory (e.g., any type of random-access memory ["RAM" ]); or persistent storage such as non-volatile memory (e.g., read-only memory ["ROM" ], power-backed RAM, flash memory, phase-change memory, etc.), a solid-state drive, a hard-disk drive, an optical-disc drive, or a portable memory device.

Unless defined otherwise, all technical and scientific terms used herein have the same meaning as commonly understood by those of ordinary skill in the art.

As set forth above, shape-sensing systems are susceptible to torsion-related distortion in the optical-fiber probes thereof, which can lead to inaccurate shape-sensing, medical decisions based thereon, and reduced patient outcomes as a result.

Disclosed herein are shape-sensing systems with vibration-assisted torsion management and methods thereof that address the foregoing. For example, a shape-sensing system can include an optical-fiber probe and a vibration-assisted torsion-management means for managing torsion in the optical-fiber probe. The optical-fiber probe can be configured to be removably disposed in an elongate medical device. The optical-fiber probe can include an inner construction and an outer construction over the inner construction but detached therefrom over a majority of the optical-fiber probe. The inner construction can include one or more optical-fiber cores disposed in a cladding. The outer construction can include a mechanical layer. The vibration-assisted torsion-management means can be operably coupled to the optical-fiber probe for vibrating either the inner construction or the outer construction of the optical-fiber probe relative to the other, which mitigates or eliminates any optical signal-distorting torsion in the inner construction of the optical-fiber probe.

These and other features of the shape-sensing systems with vibration-assisted torsion management and methods thereof will become more apparent with reference to the accompanying drawings and the following description, which provide particular embodiments of the shape-sensing systems and methods thereof in greater detail.

Shape-Sensing Systems

Figure 2:
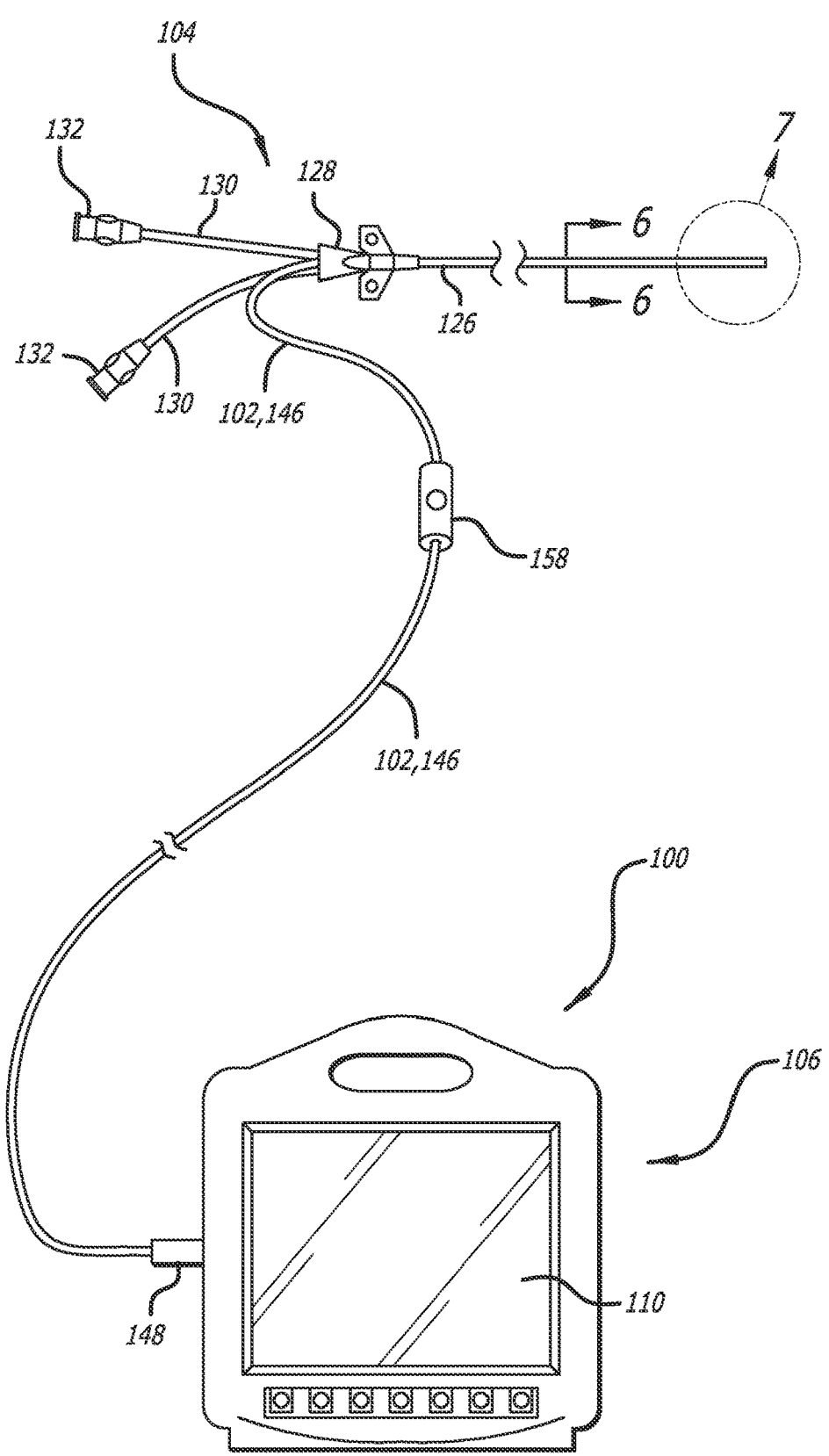
FIG. 2 illustrates a detailed view of the shape-sensing system of FIG. 1 in accordance with some embodiments.
Figures 3, 4:
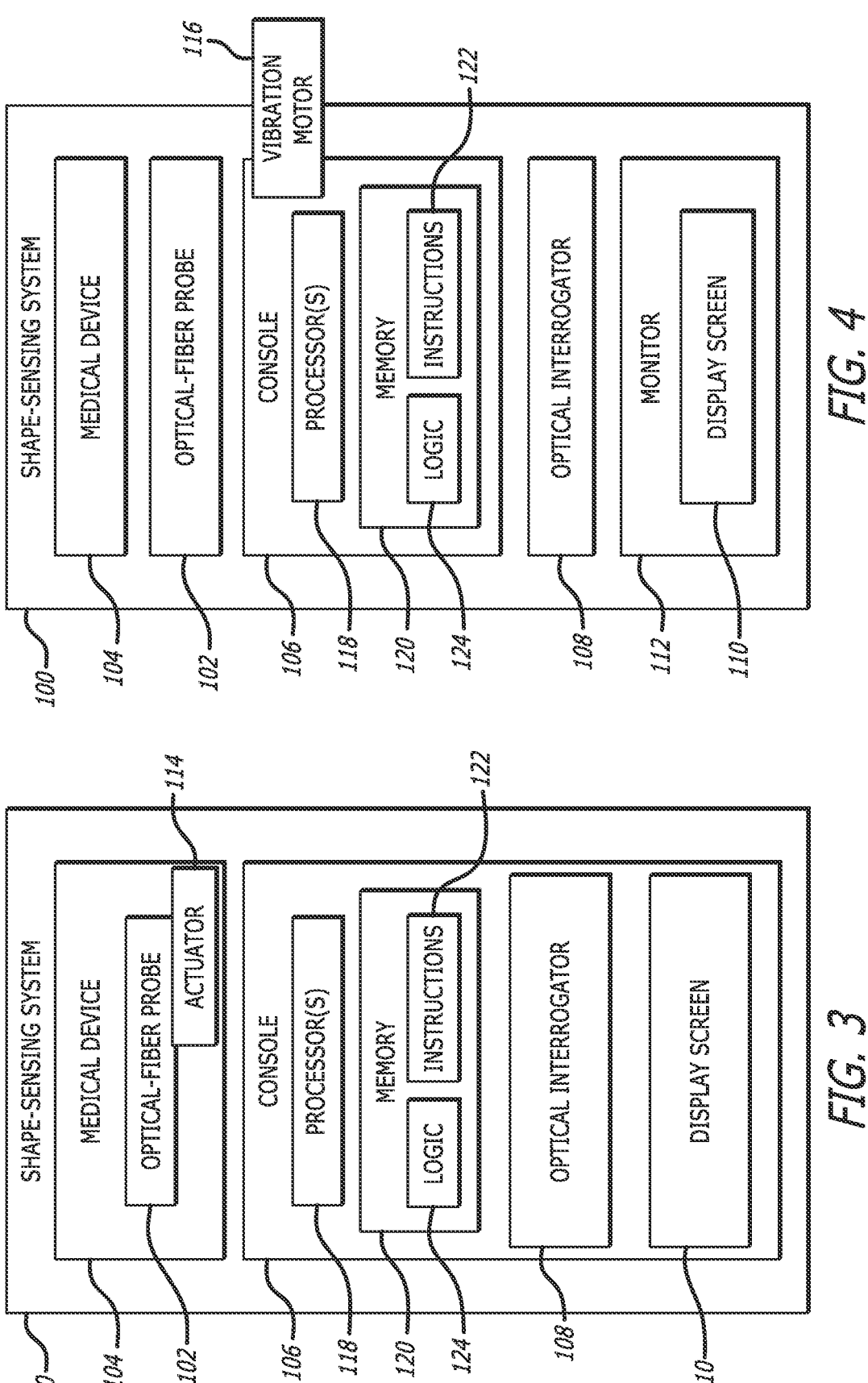
FIG. 3 illustrates a block diagram of the shape-sensing system of FIG. 1, the shape-sensing system including a number of integrated system components in accordance with some embodiments.
FIG. 4 illustrates a block diagram of another shape-sensing system including a number of separate system components in accordance with some embodiments.

FIG. 1 illustrates a shape-sensing system 100 in use on a patient P, the shape-sensing system 100 including vibration-assisted torsion management for an optical-fiber probe 102 in accordance with some embodiments, and FIG. 2 illustrates a detailed view of the shape-sensing system 100 of FIG. 1. FIGS. 3 and 4 illustrate block diagrams of the shape-sensing system 100 in accordance with at least two different embodiments thereof.

The shape-sensing system 100 can be configured for determining a shape of the optical-fiber probe 102 while the optical-fiber probe 102 is in the patient P. For example, the shape-sensing system 100 can be configured for determining the shape of the optical-fiber probe 102 during a placement procedure for placing in the patient P a medical device 104 in which the optical-fiber probe 102 is disposed, the medical device 104 including, but not limited to, an indwelling medical device such as a catheter, for example, a peripherally inserted central catheter ["PICC" ] for placement in a vasculature of the patient P. However, the shape-sensing system 100 can be further configured for determining one or more physical attributes of the patient P such as any one or more physical attributes associated with a heart (e.g., heart rate) or lungs (e.g., respiration rate) while the optical-fiber probe 102 is in the patient P. Determining the one-or-more physical attributes of the patient P is accomplished by analyzing strain experienced by the optical-fiber probe 102 in other ways than that for determining the shape of the optical-fiber probe 102. Notably, the shape-sensing system 100 can be further configured for sensing pressure, temperature, or both for the one-or-more physical attributes of the patient P. Imaging such as by optical coherence tomography (e.g., Doppler optical coherence tomography) is also possible with the shape-sensing system 100. The vibration-assisted torsion-management means for managing torsion in the optical-fiber probe 102 benefits the determining of the shape of the optical-fiber probe 102, the determining of the one-or-more physical attributes of the patient P, or even imaging with the shape-sensing system 100 as set forth below.

As shown, the shape-sensing system 100 can include one or more system components selected from a console 106, an optical interrogator 108, the medical device 104, the optical-fiber probe 102, and a vibration-assisted torsion-management means for managing torsion in the optical-fiber probe 102. Indeed, each figure of FIGS. 1-4 shows such a shape-sensing system 100; however, the shape-sensing system 100 of FIGS. 1-3 is shown with more integrated system components than that of FIG. 4, and the shape-sensing system 100 of FIG. 4 is shown with more separate system components than that of FIGS. 1-3. For example, FIG. 3 shows the shape-sensing system 100 can include the console 106 and the medical device 104, wherein the console 106 can include both the optical interrogator 108 and a display screen 110 integrated in the console 106, and the medical device 104 can include the optical-fiber probe 102 integrated in the medical device 104. Differently, FIG. 4 shows the shape-sensing system 100 can include the console 106, the optical interrogator 108, and a monitor 112 including the display screen 110 as separate system components. In addition, the medical device 104 and the optical-fiber probe 102 can be separate system components with the optical-fiber probe 102 configured to be removably disposed in the medical device 104. Notably, the vibration-assisted torsion-management means can be associated with the console 106, the optical-fiber probe 102, or both. Indeed, FIG. 3 shows an actuator 114 for the vibration-assisted torsion-management means associated with the optical-fiber probe 102, and FIG. 4 shows a vibration motor 116 for the vibration-assisted torsion-management means associated with the console 106. It should be understood that the shape-sensing system 100 is not limited to that of either FIG. 3 or FIG. 4; the shape-sensing system 100 can include any combination of the integrated and separated system components shown in FIGS. 3 and 4.

The console 106 can include one or more processors 118, memory 120, and executable instructions 122 stored in the memory 120 that, upon execution of the instructions 122 by the one-or-more processors 118, cause the console 106 to perform a set of operations including determining the shape of the optical-fiber probe 102 in the patient P, determining the one-or-more physical attributes of the patient P, vibrating the vibration-assisted torsion-management means, or a combination thereof. For example, the set of operations can include receiving FBG sensor-reflected optical signals from the optical interrogator 108; converting the FBG sensor-reflected optical signals into converted electrical signals with the optical signal-converter logic, and determining, in real time, the shape of the optical-fiber probe 102 from the converted electrical signals with the shape-sensing logic of the console 106. (See, e.g., Floris, Ignazio, et al. "Fiber optic shape sensors: A comprehensive review." *Optics and Lasers in Engineering* 139 (2021): 106508, which is incorporated by reference in its entirety into this application for details in the determining of the shape of the optical-fiber probe 102 from the FBG sensor-reflected optical signals from the optical interrogator 108.) Optionally, the shape of the optical-fiber probe 102 is determined while vibrating the vibration-assisted torsion-management means to release any torsion in the optical-fiber probe 102 for a more accurate determination of the shape of the optical-fiber probe 102. In addition, the set of operations can further include tracking the vibrating of the optical-fiber probe 102 by the vibration-assisted torsion-management means with vibration-tracking logic of the console 106; and removing from the converted electrical signals any portion thereof related to vibrations by the vibration-assisted torsion-management management means for the shape of the optical-fiber probe 102 or the one-or-more physical attributes of the patient P. Notably, the vibrations by the vibration-assisted torsion-management management means can have a signature such as a certain periodicity, thereby facilitating removal of noise corresponding to the vibrations from the converted electrical signals.

As alluded to above, the console 106 can also include logic 124 selected from at least optical signal-converter logic, shape-sensing logic, physical attribute-determination logic, torsion-detection logic, speech-recognition logic, and vibration-tracking logic.

The optical signal-converter logic can be configured to convert, in real time, the FBG sensor-reflected optical signals received from the optical interrogator 108 into the converted electrical signals.

The shape-sensing logic can be configured to determine, in real time, the shape of the optical-fiber probe 102 from the converted electrical signals for display on the display screen 110. (See, for example, the plot for the optical-fiber probe 102 on the display screen 110 of the console 106 of FIG. 1.) When the shape of the optical-fiber probe 102 is indicative of the optical-fiber probe 102 encountering or being present in more tortured vasculature or the like, the shape-sensing logic can be further configured to send a signal to start the vibration-assisted torsion-management means.

The physical attribute-determination logic can be configured to determine, in real time, the one-or-more physical attributes of the patient P from the converted electrical signals for display on the display screen 110. For example, the physical attribute-determination logic can be configured to determine the heart rate or the respiration rate of the patient P from simple or compound oscillations present in the converted electrical signals from the heart or lungs of the patient beating or respiring.

The torsion-detection logic can be configured to detect, in real time, any torsion in the optical-fiber probe 102 from the converted electrical signals. When the torsion in the optical-fiber probe 102 exceeds a pre-determined threshold, the torsion-detection logic can be further configured to send a signal to start the vibration-assisted torsion-management means.

The speech-recognition logic can be configured to recognize speech, in real time, for any spoken commands received by a microphone of the console 106. When the speech-recognition logic recognizes a spoken command for starting or stopping the vibration-assisted torsion-management means, the speech-recognition logic can be further configured to send a signal to start or stop the vibration-assisted torsion-management means.

The vibration-tracking logic can be configured to track, in real time, any vibrations in the optical-fiber probe 102 by the vibration-assisted torsion-management means. The optical signal-converter logic, in cooperation with the vibration-tracking logic, can be further configured to remove from the converted electrical signals any portion thereof related to the vibrations by the vibration-assisted torsion-management management means for the shape of the optical-fiber probe 102 or the one-or-more physical attributes of the patient P.

The optical interrogator 108 can be configured to send input optical signals (e.g., 1460-1620 nm laser light by way of a tunable laser) into the optical-fiber probe 102 and receive the FBG sensor-reflected optical signals from the optical-fiber probe 102. Again, the optical interrogator 108 can be integrated in the console 106 as shown in FIG. 3, or the optical interrogator 108 can be a separate system component.

The display screen 110 can be configured to display output for the shape-sensing system 100. Such output can include graphical output such as a plot of the shape of the optical-fiber probe 102, textual output such as that for the one-or-more physical attributes of the patient P, or a combination thereof. For example, the display screen 110 integrated into the console 106 of FIG. 1 is shown displaying the plot of the shape of the optical-fiber probe 102 over a 3-dimensional grid, which shape represents the optical-fiber probe 102—and the PICC embodiment of the medical device 104 in which it is disposed—in a superior vena cava ("SVC") of the patient P. While not shown, the one-or-more physical attributes, too, can be shown in one or more plots to facilitate historical analysis before, during, and after a procedure such as the placement procedure for placing the PICC embodiment of the medical device 104. Again, the display screen 110 can be integrated in the console 106 as shown in FIG. 1, or the display screen 110 can be in a separate system component such as the monitor 112.

Medical Devices

Figure 5:
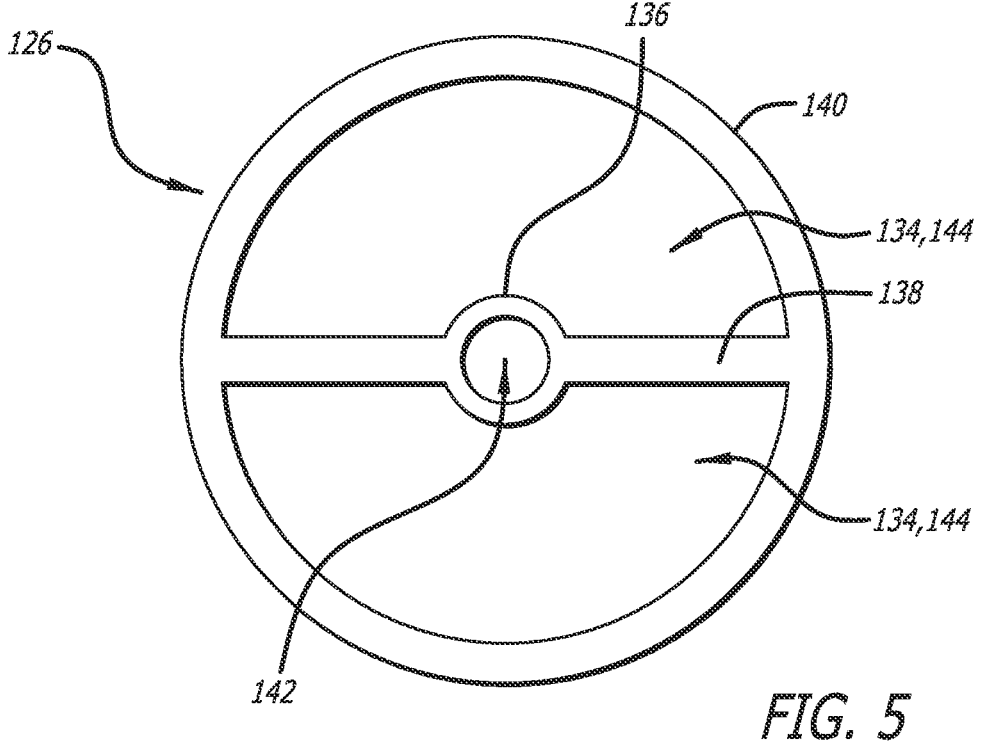
FIG. 5 illustrates a transverse cross-section of a catheter tube of a catheter of the shape-sensing system, the catheter without a removable optical-fiber probe for shape-sensing in accordance with some embodiments.
Figure 6:
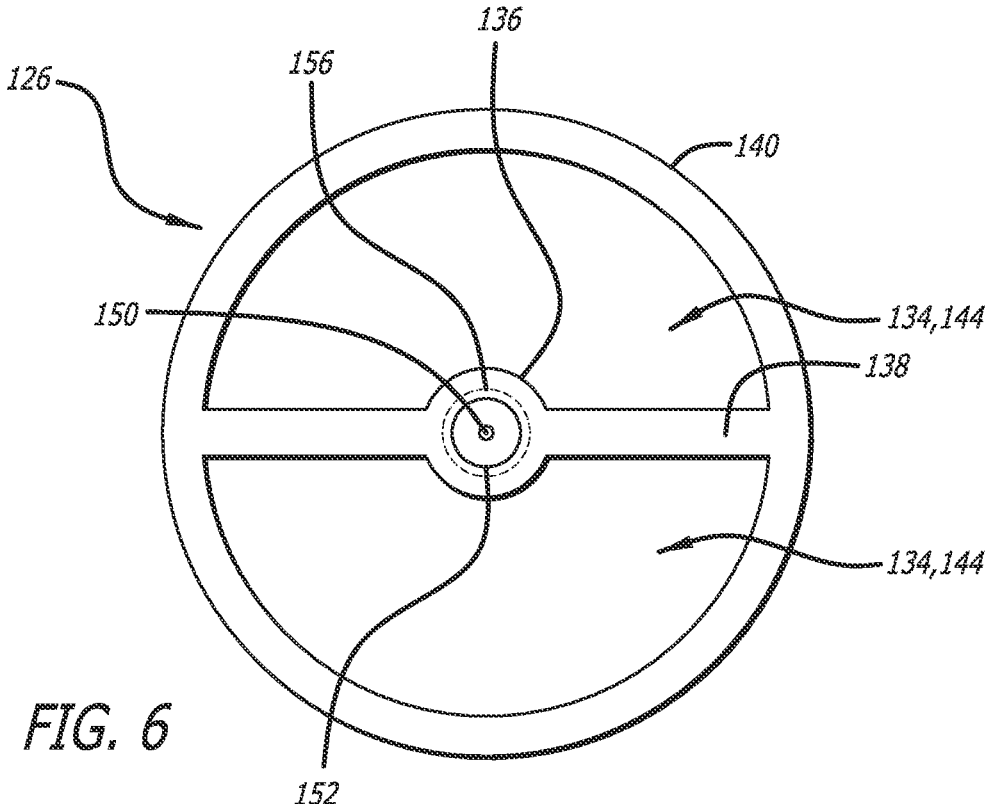
FIG. 6 illustrates a transverse cross-section of a catheter tube of a catheter of the shape-sensing system, the catheter including the removable optical-fiber probe or an integrated optical-fiber probe for shape-sensing in accordance with some embodiments.

FIG. 1 illustrates the shape-sensing system 100 in use on the patient P, the shape-sensing system 100 including a PICC as the medical device 104 in accordance with some embodiments. FIGS. 5 and 6 illustrate transverse cross-sections of a catheter tube 126 of the PICC embodiment of the medical device 104 in accordance with some embodiments, while FIG. 7 illustrates a longitudinal cross-section of the catheter tube 126 of the PICC embodiment of the medical device 104 in accordance with some embodiments.

The PICC embodiment of the medical device 104 can include the catheter tube 126, a furcated hub 128 such as a bifurcated hub, a corresponding number of extension legs 130 such as a pair of extension legs, and a corresponding number of Luer 132 connectors such as a pair of Luer connectors fluidly connected in the foregoing order.

Figure 7:
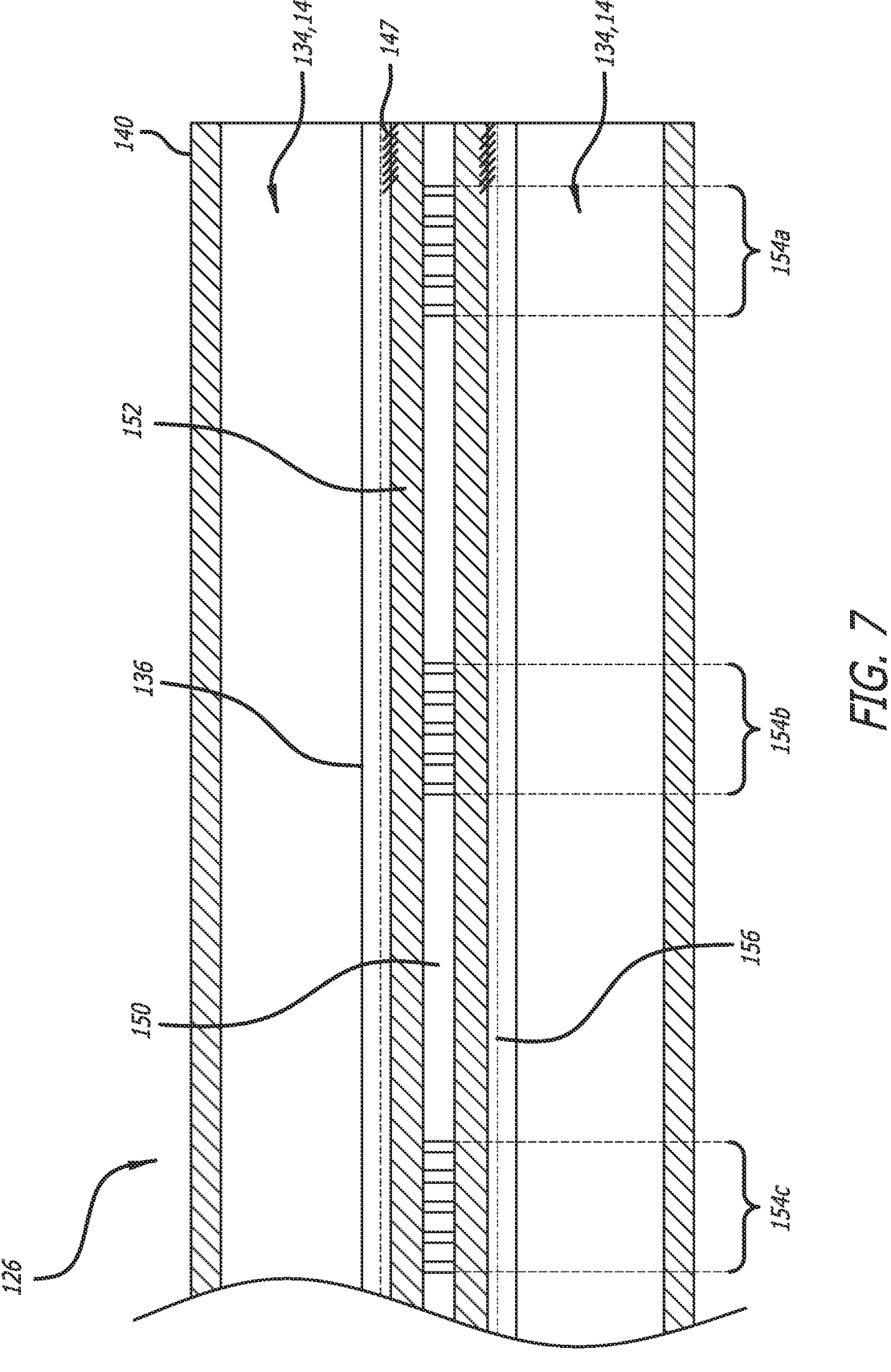
FIG. 7 illustrates a longitudinal cross-section of the catheter tube of the catheter, the catheter including the removable or integrated optical-fiber probe in accordance with some embodiments.

The catheter tube 126 can include a number of catheter-tube lumens 134 corresponding to the number of extension legs 130 such as the pair of catheter-tube lumens shown in FIGS. 5-7. When the optical-fiber probe 102 is integrated in the PICC embodiment of the medical device 104, the optical-fiber probe 102 can be integrated in a longitudinal bead 136 extruded with the catheter tube 126 such as the bead 136 shown in FIGS. 5-7, which bead 136 is in a middle of a septum 138 dividing luminal space of the catheter tube 126 into the number of catheter-tube lumens 134. However, such a bead 136 can alternatively be located closer to a catheter wall 140 of the catheter tube 126 such as on the catheter wall 140 while still being in the septum 138. The bead 136 can even be separate from the septum 138 such as on the catheter wall 140 or in the catheter wall 140 of the catheter tube 126. Notably, when the optical-fiber probe 102 is removable, the optical-fiber probe 102 can be disposed in any lumen of the PICC embodiment of the medical device 104 or a bead-based conduit 142 thereof configured for the optical-fiber probe 102. Unlike the number of catheter lumens 144 extending through the PICC embodiment of the medical device 104, the conduit 142 need not extend through an extension leg. Indeed, the conduit 142 can extend through the catheter tube 126 and furcated hub 128, from which furcated hub 128 the extension tube 146 can extend, or into which furcated hub 128 the optical-fiber probe 102 can be removably inserted.

The furcated hub 128 can have a number of hub lumens corresponding to the number of catheter-tube lumens 134, with the number of hub lumens fluidly connected to the number of catheter-tube lumens 134.

Each extension leg of the number of extension legs 130 can have an extension-leg lumen fluidly connected to a hub lumen of the number of hub lumens. With the number of hub lumens fluidly connected to the number of catheter-tube lumens 134, and with the number of extension-leg lumens fluidly connected to the number of hub lumens, a number of catheter lumens 144 can extend through an entirety of the PICC embodiment of the medical device 104.

The PICC embodiment of the medical device 104 can further include an extension tube 146 extending from the furcated hub 128. The extension tube 146 can be a skived portion of the catheter tube 126 skived down to the bead 136 and optical-fiber probe 102, or the extension tube 146 can be another tube in which the foregoing skived portion of the catheter tube 126 is disposed, either of which can terminate in the probe-side connector 148 for establishing the optical connection between the optical fiber of the optical-fiber probe 102 and that of the optical interrogator 108, whether the optical interrogator 108 is a separate component of the shape-sensing system 100 or integrated in the console 106.

While the PICC is provided as a particular embodiment of the medical device 104 of the shape-sensing system 100, it should be understood that any medical device of a number of medical devices can include the optical-fiber probe 102, whether the optical-fiber probe 102 is integrated in the medical device 104 or removably disposed in the medical device 104. This includes other central venous catheters, which can include similar features as the PICC such as the fluidly connected catheter tube 126, furcated hub 128, and number of extension legs 130.

Optical-Fiber Probes

FIG. 1 illustrates the shape-sensing system 100 in use on the patient P, the shape-sensing system 100 including the optical-fiber probe 102 in accordance with some embodiments. FIGS. 6 and 7 respectively illustrate the transverse cross-section and the longitudinal cross-section of the catheter tube 126 of the PICC embodiment of the medical device 104, which PICC includes the optical-fiber probe 102 in accordance with some embodiments.

As set forth above, the optical-fiber probe 102 can be integrated in the medical device 104 such as by extrusion of the catheter tube 126 thereover, or the optical-fiber probe 102 can be a separate component configured to be removably disposed in the conduit 142 or any lumen of the medical device 104. Whether integrated in the medical device 104 or separate therefrom, the optical-fiber probe 102 can include an inner construction and an outer construction over the inner construction, wherein the outer construction encases the inner construction but is detached therefrom over a majority of the optical-fiber probe 102. For example, the outer construction can be coupled to the inner construction by a coupling 147 (e.g., interlocking connection, bond, etc.) in a distal-end portion of the optical-fiber probe 102, within a probe-side connector 148 about a proximal-end portion of the optical-fiber probe 102 by a same or different coupling, or both. Notably, the connector can be configured for establishing an optical connection between the optical fiber of the optical-fiber probe 102 and that of the optical interrogator 108, whether the optical interrogator 108 is a separate component of the shape-sensing system 100 or integrated in the console 106.

The inner construction of the optical-fiber probe 102 can include one or more optical-fiber cores 150 disposed in a cladding 152, wherein each optical-fiber core of the one-or-more optical-fiber cores 150 can have a relatively smaller diameter configured for a single mode of light propagation or a relatively larger diameter configured for multiple modes of light propagation. In an example, the optical-fiber probe 102 can include a single core configured for a single mode of light propagation or a single core configured for multiple modes of light propagation, as shown in FIGS. 6 and 7. In another example, the optical-fiber probe 102 can include a number of cores such as three, seven, thirteen, nineteen, or more cores configured for a single mode of light propagation, multiple modes of light propagation, or a combination of the foregoing modes of light propagation.

Each optical-fiber core of the one-or-more optical-fiber cores 150 of the inner construction can include a number of FBG sensors 154a, 154b, 154c, . . . , 154n along at least a distal portion of the optical-fiber probe 102 configured for shape sensing with the shape-sensing system 100. The FBG sensors 154a, 154b, 154c, . . . , 154n can include variations in refractive index of the optical-fiber core, thereby forming wavelength-specific reflectors of the FBG sensors 154a, 154b, 154c, . . . , 154n configured to reflect the input optical signals sent into the optical-fiber probe 102 by the optical interrogator 108. FIG. 7 illustrates, in particular, a last three FBG sensors 154a, 154b, and 154c in the distal portion of the optical-fiber probe 102, which FBG sensors 154a, 154b, and 154c can be particularly useful for the shape-sensing logic when determining whether the optical-fiber probe 102 is encountering more tortured vasculature or the like for subsequently sending the signal to start the vibration-assisted torsion-management means. This is because the last three FBG sensors 154a, 154b, and 154c firstly and directly experience a physical change in curvature of the optical-fiber probe 102 when encountering the more tortured vasculature or the like.

The outer construction of the optical-fiber probe 102 can include a mechanical layer 156, which can be tubing over the inner construction of the optical-fiber probe 102 but substantially detached therefrom as set forth above. The tubing can be metal tubing such as tubing of nitinol or stainless steel, or the tubing can be polymer tubing such as tubing of a thermoplastic elastomer, for example, a polyether block amide. The polymer tubing can include one or more metal wires disposed in the polymer tubing. The one-or-more metal wires can be configured to provide additional structural support to the polymer tubing. For example, a number of metal wires can be braided into a braided sleeve over which the polymer tubing is extruded, the braided sleeve or the number of metal wires providing the additional structural support to the polymer tubing. The one-or-more metal wires can additionally or alternatively be configured to convey electrical signals such as electrocardiogram ("ECG") signals over a length of the optical-fiber probe 102. Such ECG signals can provide ECG data complementary to FBG-sensor data for determining at least the one-or-more physical attributes of the patient P. Notably, the metal tubing can be likewise configured to convey the electrical signals over the length of the optical-fiber probe 102 and provide the complementary ECG data complementary for determining at least the one-or-more physical attributes of the patient P.

Vibration-Assisted Torsion Management

FIGS. 8-11 illustrate various vibration-assisted torsion-management means for managing torsion in the optical-fiber probe 102 in accordance with some embodiments.

The vibration-assisted torsion-management means can be operably coupled to the optical-fiber probe 102 for vibrating either the inner construction or the outer construction of the optical-fiber probe 102 relative to the other, which mitigates or eliminates any optical signal-distorting torsion in the inner construction of the optical-fiber probe 102. Notably, internal friction between the inner construction and the outer construction of the optical-fiber probe 102 that otherwise maintains any induced torsion in the optical-fiber probe 102 is reduced through vibrations with the vibration-assisted torsion-management means. Indeed, the dynamic coefficient of friction between the inner construction and the outer construction of the optical-fiber stylet operative during the vibrations is less than the static coefficient of friction between the inner construction and the outer construction of the optical-fiber stylet in the absence of the vibrations, which facilitates release of any torsion in the optical-fiber probe 102 with the vibrations.

Figures 8, 9:
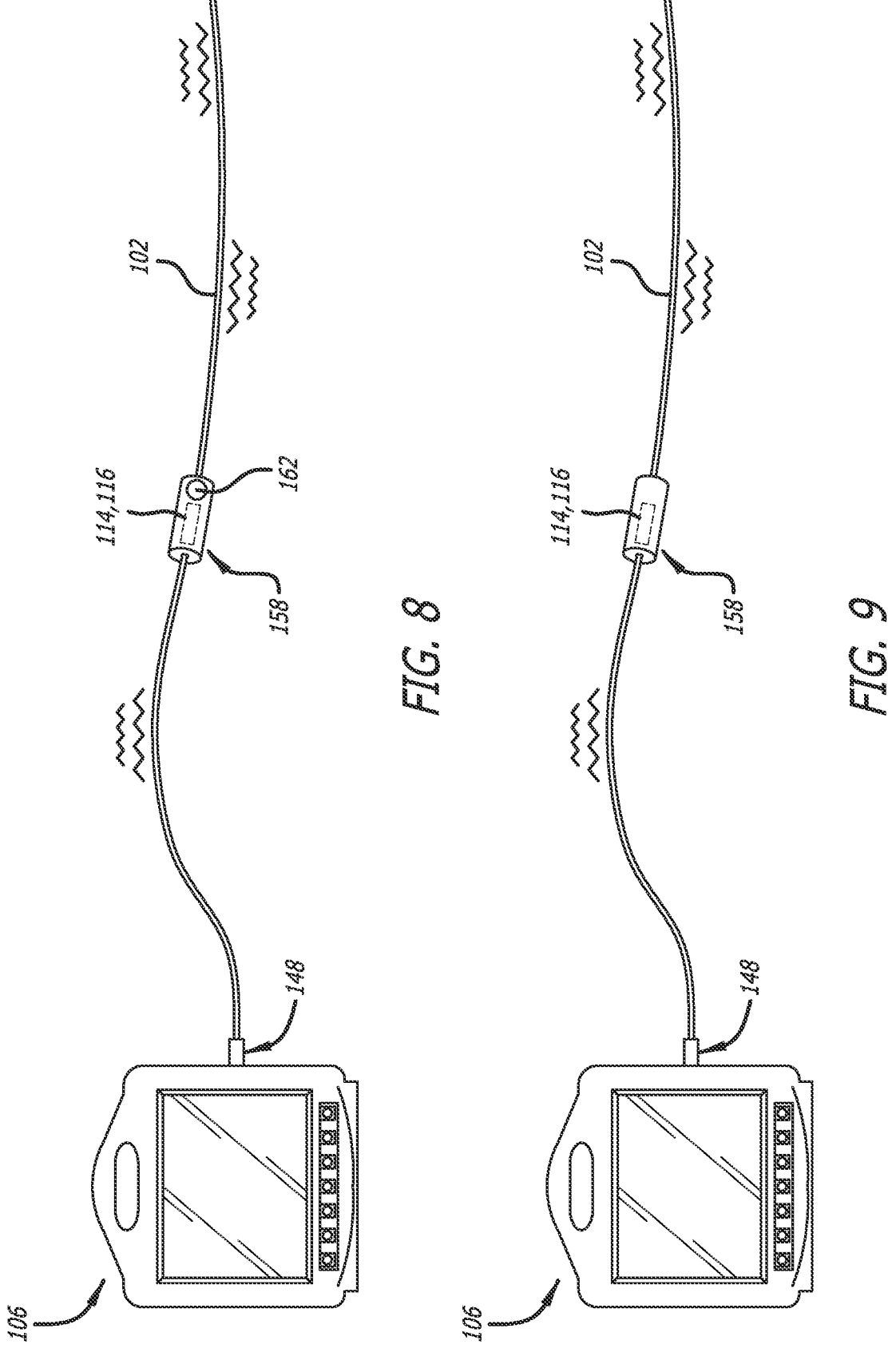
FIG. 8 illustrates a first vibration-assisted torsion-management means for managing torsion in the optical-fiber probe in accordance with some embodiments.
FIG. 9 illustrates a second vibration-assisted torsion-management means for managing torsion in the optical-fiber probe in accordance with some embodiments.
Figures 10, 11:
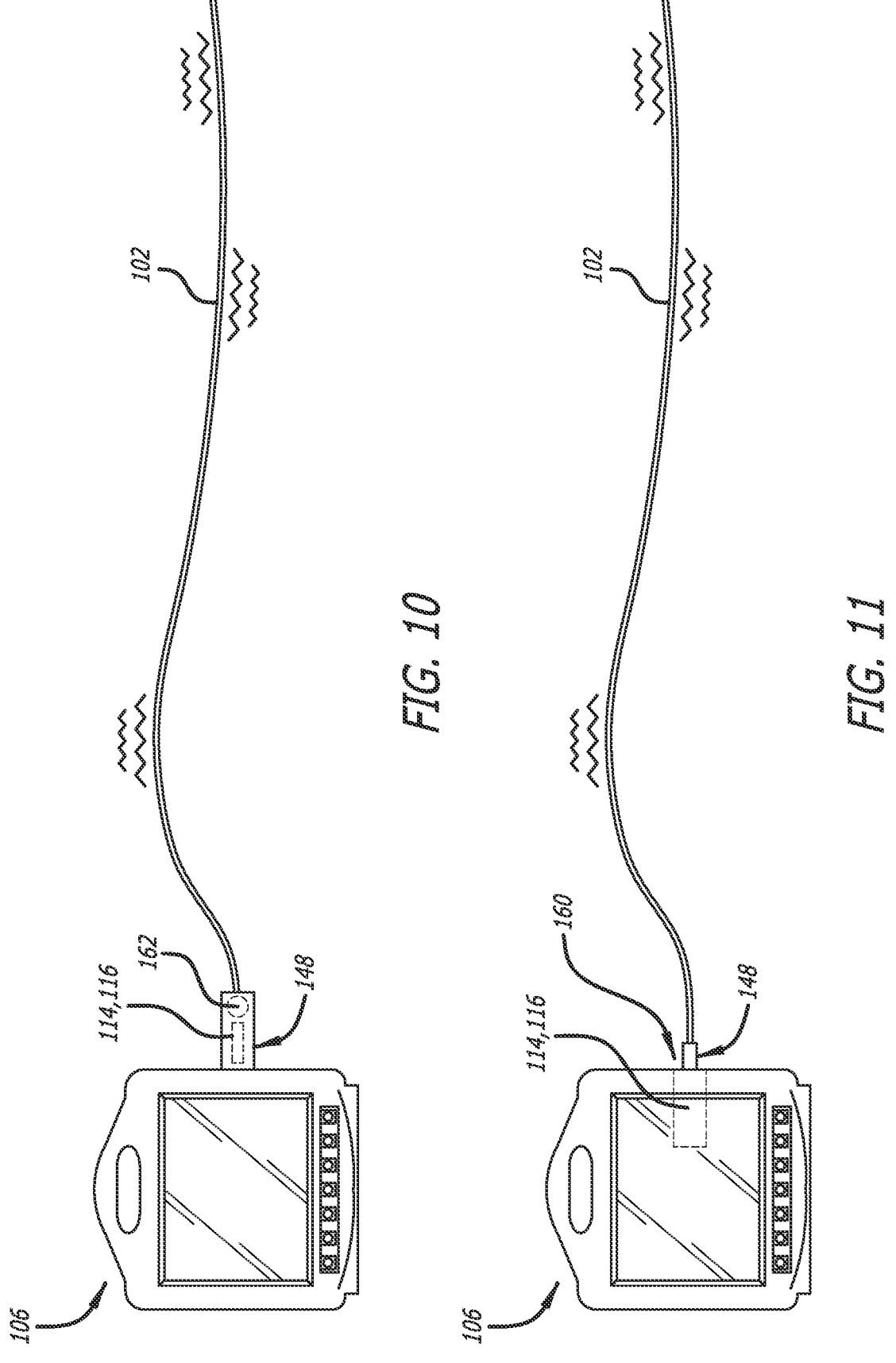
FIG. 10 illustrates a third vibration-assisted torsion-management means for managing torsion in the optical-fiber probe in accordance with some embodiments.
FIG. 11 illustrates a fourth vibration-assisted torsion-management means for managing torsion in the optical-fiber probe in accordance with some embodiments.

The vibration-assisted torsion-management means can include the vibration motor 116 or actuator 114 operably coupled to the optical-fiber probe 102 for vibrating either the inner construction or the outer construction of the optical-fiber probe 102 relative to the other. The vibration motor 116 or actuator 114 can be disposed in or around a handle 158 about a proximal portion of the optical-fiber probe 102 as shown in FIGS. 8 and 9, the probe-side connector 148 about the proximal-end portion of the optical-fiber probe 102 as shown in FIG. 10, or another component of the shape-sensing system 100 proximal of the probe-side connector 148 of the optical-fiber probe 102. For example, the other component of the shape-sensing system 100 can be associated with a console-side connector 160 in the console 106 for the optical-fiber probe 102 as shown in FIG. 11. The console-side connector 160 can be configured to transfer vibrations to the optical-fiber probe 102 through the probe-side connector 148 of the optical-fiber probe 102. Such a vibration motor 116 or actuator 114 can be selected from at least an eccentric rotating-mass vibration motor, a linear resonant actuator, and a solenoid actuator. In some examples, the vibration-assisted torsion-management means can include a linear resonant actuator or a solenoid actuator in or around the handle 158 about the proximal portion of the optical-fiber probe 102 as shown in FIGS. 8 and 9, an eccentric rotating-mass vibration motor, a linear resonant actuator, or a solenoid actuator in or around the probe-side connector 148 about the proximal-end portion of the optical-fiber probe 102 as shown in FIG. 10, or an eccentric rotating-mass vibration motor in or around the console-side connector 160 of the optical-fiber probe 102 as shown in FIG. 11.

The vibration-assisted torsion-management means can be configured to constantly vibrate while the shape-sensing system 100 is in use, or the vibration-assisted torsion-management means can be configured to start or stop as wanted or needed. For example, the vibration motor 116 or actuator 114 embodiments of the vibration-assisted torsion-management means can be configured to start or stop by a switch 162 (e.g., flip switch, slide switch, push button, etc.) when the vibration motor 116 or actuator 114 is part of the handle 158 or the probe-side connector 148 as shown in FIGS. 8 and 10. However, the vibration motor 116 or actuator 114 can likewise be configured to start or stop by the switch 162 (e.g., on-screen button on the display screen 110) when the vibration motor 116 or actuator 114 is part of the console 106 such in or around the console-side connector 160 of the optical-fiber probe 102 as shown in FIG. 11.

Further to the vibration-assisted torsion-management means being configured to start or stop as wanted or needed, the console 106 can be configured through one or more program settings or the logic 124 to start or stop the vibration motor 116 or actuator 114 embodiments of the vibration-assisted torsion-management means, optionally through wired or wireless communications with the vibration motor 116 or actuator 114 when the vibration motor 116 or actuator 114 is part of the handle 158 (see FIG. 9) or the probe-side connector 148 of the optical-fiber probe 102 (see FIG. 10). The one-or-more program settings can be set to start or stop the vibration motor 116 or actuator 114 at predetermined times or locations of a distal tip the optical-fiber probe 102 during a placement procedure for placing the medical device 104 in the patient P. As to the logic 124, the shape-sensing logic, the torsion-detection logic, or both can be configured to send a signal to start or stop the vibration motor 116 or actuator 114. For example, the shape-sensing logic can be configured to send a signal to start the vibration motor 116 or actuator 114 when the shape of the optical-fiber probe 102 is indicative of the optical-fiber probe 102 encountering or being present in more tortured vasculature or the like, as determined by a threshold rate of increase in a bending radius of the optical-fiber probe 102 or an instant bending radius of the optical-fiber probe 102. When the shape of the optical-fiber probe 102 is indicative of the optical-fiber probe 102 exiting the more tortured vasculature or the like, the shape-sensing logic can be configured to send a signal to stop the vibration motor 116 or actuator 114. Likewise, the torsion-detection logic can be configured to send a signal to start the vibration motor 116 or actuator 114 when a rate of increase in the torsion in the optical-fiber probe 102 or an instant torsion in the optical-fiber probe 102 exceeds a pre-determined threshold therefor. When the rate of increase or the instant torsion in the optical-fiber probe 102 falls below the pre-determined threshold therefor, the torsion-detection logic can be configured to send a signal to stop the vibration motor 116 or actuator 114. Lastly, the speech-recognition logic can be configured to send a signal to start or stop the vibration motor 116 or actuator 114 when a spoken command for starting or stopping the vibration-assisted torsion-management means is recognized.

The vibration-assisted torsion-management means can be further configured for haptic feedback to indicate the torsion in the optical-fiber probe 102 exceeds the pre-determined threshold therefor, kinking of the optical-fiber probe 102, or damage to the optical-fiber probe 102 other than kinking. The vibration-assisted torsion-management means can be even further configured such that the haptic feedback indicates excessive force in advancing the optical-fiber probe 102 in vasculature or the like, obstructions in advancing the optical-fiber probe 102 in the foregoing, or the like.

Methods

Methods can include methods of the shape-sensing system 100. For example, a method of the shape-sensing system 100 can include one or more steps selected from an optical signal-sending step, an optical signal-receiving step, an optical probe-vibrating step, a vibration-tracking step, an optical signal-converting step, a vibration signal-removing step, and a shape-determining step.

The optical signal-sending step can include sending the input optical signals into the optical-fiber probe 102 with the optical interrogator 108 while the optical-fiber probe 102 is advanced through the vasculature of the patient P. As set forth above, the optical-fiber probe 102 can include the inner construction and the outer construction over the inner construction but detached therefrom over the majority of the optical-fiber probe 102. The inner construction can include the one-or-more optical-fiber cores 150 disposed in the cladding 152. The outer construction can include the mechanical layer 156 of tubing such as the metal tubing, the polymer tubing, or the polymer tubing including the one-or-more metal wires disposed in the polymer tubing.

The optical signal-receiving step can include receiving the reflected optical signals from the optical-fiber probe 102 with the optical interrogator 108.

The optical probe-vibrating step can include vibrating either the inner construction or the outer construction of the optical-fiber probe 102 relative to the other with the vibration-assisted torsion-management means operably coupled to the optical-fiber probe 102. The vibration-assisted torsion-management means can manage torsion in the optical-fiber probe 102 while the optical-fiber probe 102 is advanced through the vasculature.

The optical probe-vibrating step can include vibrating the optical-fiber probe 102 with the vibration motor 116 or the actuator 114 operably coupled to the optical-fiber probe 102. The vibration motor 116 or actuator 114 can be selected from the eccentric rotating-mass vibration motor, the linear resonant actuator, and the solenoid actuator.

The vibration-tracking step can include tracking the vibrating of the optical-fiber probe 102 by the vibration-assisted torsion-management means with the vibration-tracking logic of the console 106.

The optical signal-converting step can include converting the reflected optical signals into the converted electrical signals with the optical signal-converter logic of the console 106 including the optical interrogator 108 or operably connected thereto.

The vibration signal-removing step can include removing from the converted electrical signals any portion thereof related to vibration-assisted torsion management for at least the shape of the optical-fiber probe 102.

The shape-determining step can include determining, in real time, at least the shape of the optical-fiber probe 102 from the converted electrical signals with the shape-sensing logic of the console 106.

While some particular embodiments have been disclosed herein, and while the particular embodiments have been disclosed in some detail, it is not the intention for the particular embodiments to limit the scope of the concepts provided herein. Additional adaptations or modifications can appear to those of ordinary skill in the art, and, in broader aspects, these adaptations or modifications are encompassed as well. Accordingly, departures may be made from the particular embodiments disclosed herein without departing from the scope of the concepts provided herein.

What is claimed is:

1. A shape-sensing system, comprising:
an optical-fiber probe configured to be removably disposed in an elongate medical device, the optical-fiber probe including:
an inner construction of one or more optical-fiber cores disposed in a cladding; and
an outer construction including a mechanical layer over the inner construction but detached therefrom over a majority of the optical-fiber probe; and
a vibration-assisted torsion-management means for managing torsion in the optical-fiber probe, the vibration-assisted torsion-management means operably coupled to the optical-fiber probe for vibrating the inner construction relative to the outer construction of the optical-fiber probe or vibrating the outer construction relative to the inner construction of the optical-fiber probe to mitigate or eliminate any optical signal-distorting torsion in the inner construction of the optical-fiber probe,
wherein the vibration-assisted torsion-management means includes a vibration motor or an actuator disposed in a handle about a proximal portion of the optical-fiber probe and operably coupled to the optical-fiber probe, the vibration motor or actuator selected from an eccentric rotating-mass vibration motor, a linear resonant actuator, and a solenoid actuator.

2. The shape-sensing system of claim 1, wherein the mechanical layer is metal tubing.

3. The shape-sensing system of claim 2, wherein the metal tubing is configured to convey electrical signals along a length of the optical-fiber probe.

4. The shape-sensing system of claim 1, wherein the mechanical layer is polymer tubing.

5. The shape-sensing system of claim 4, wherein the mechanical layer includes one or more metal wires disposed in the polymer tubing.

6. The shape-sensing system of claim 5, wherein the one or more metal wires are configured to convey electrical signals along a length of the optical-fiber probe.

7. The shape-sensing system of claim 1, wherein the vibration motor or the actuator is started by a switch of the handle.

8. The shape-sensing system of claim 1, wherein each fiber core of the one or more fiber cores of the optical-fiber probe include a number of fiber Bragg grating ("FBG") sensors along at least a distal portion of the optical-fiber probe.

9. The shape-sensing system of claim 8, further comprising:

an optical interrogator configured to send input optical signals into the optical-fiber probe and receive FBG sensor-reflected optical signals from the optical-fiber probe; and a console including one or more processors, memory, and executable instructions stored in the memory that cause the console to perform a set of operations upon execution of the executable instructions by the one or more processors, the set of operations including:

receiving the FBG sensor-reflected optical signals from the optical interrogator;

converting the FBG sensor-reflected optical signals into converted electrical signals with optical signal-converter logic of the console; and determining, in a real-time determination, at least a shape of the optical-fiber probe from the converted electrical signals with shape-sensing logic of the console.

10. The shape-sensing system of claim 9, wherein the set of operations further includes:

tracking vibrating of the optical-fiber probe by the vibration-assisted torsion-management means with vibration-tracking logic of the console; and removing from the converted electrical signals any portion thereof related to vibration-assisted torsion management for at least the shape of the optical-fiber probe.

11. A shape-sensing system, comprising:

an optical-fiber probe configured to be removably disposed in an elongate medical device, the optical-fiber probe including:

an inner construction of one or more optical-fiber cores disposed in a cladding; and an outer construction including a mechanical layer over the inner construction but detached therefrom over a majority of the optical-fiber probe; and a vibration-assisted torsion-management means for managing torsion in the optical-fiber probe, the vibration-assisted torsion-management means operably coupled to the optical-fiber probe for vibrating the inner construction relative to the outer construction of the optical-fiber probe or vibrating the outer construction relative to the inner construction of the optical-fiber probe to mitigate or eliminate any optical signal-distorting torsion in the inner construction of the optical-fiber probe, wherein the vibration-assisted torsion-management means includes a vibration motor or an actuator disposed in a probe-side connector about a proximal-end portion of the optical-fiber probe and operably coupled to the optical-fiber probe, the vibration motor or the actuator selected from an eccentric rotating-mass vibration motor, a linear resonant actuator, and a solenoid actuator.

12. The shape-sensing system of claim 11, wherein the vibration motor or the actuator is started by a switch of the probe-side connector of the optical-fiber probe.

13. The shape-sensing system of claim 11, wherein each fiber core of the one or more fiber cores of the optical-fiber probe include a number of fiber Bragg grating ("FBG") sensors along at least a distal portion of the optical-fiber probe.

14. The shape-sensing system of claim 13, further comprising:

an optical interrogator configured to send input optical signals into the optical-fiber probe and receive FBG sensor-reflected optical signals from the optical-fiber probe; and a console including one or more processors, memory, and executable instructions stored in the memory that cause the console to perform a set of operations upon execution of the executable instructions by the one or more processors, the set of operations including:

receiving the FBG sensor-reflected optical signals from the optical interrogator;

converting the FBG sensor-reflected optical signals into converted electrical signals with optical signal-converter logic of the console; and determining, in a real-time determination, at least a shape of the optical-fiber probe from the converted electrical signals with shape-sensing logic of the console.

15. The shape-sensing system of claim 14, wherein the set of operations further includes:

tracking vibrating of the optical-fiber probe by the vibration-assisted torsion-management means with vibration-tracking logic of the console; and removing from the converted electrical signals any portion thereof related to vibration-assisted torsion management for at least the shape of the optical-fiber probe.

16. A shape-sensing system, comprising:

an optical-fiber probe configured to be removably disposed in an elongate medical device, the optical-fiber probe including:

an inner construction of one or more optical-fiber cores disposed in a cladding; and an outer construction including a mechanical layer over the inner construction but detached therefrom over a majority of the optical-fiber probe; and a vibration-assisted torsion-management means for managing torsion in the optical-fiber probe, the vibration-assisted torsion-management means operably coupled to the optical-fiber probe for vibrating the inner construction relative to the outer construction of the optical-fiber probe or vibrating the outer construction relative to the inner construction of the optical-fiber probe to mitigate or eliminate any optical signal-distorting torsion in the inner construction of the optical-fiber probe, wherein:

the vibration-assisted torsion-management means includes a vibration motor or an actuator operably coupled to the optical-fiber probe, the vibration motor or the actuator selected from an eccentric rotating-mass vibration motor, a linear resonant actuator, and a solenoid actuator; and the vibration motor or the actuator is disposed in another component of the shape-sensing system proximal of a probe-side connector about a proximal-end portion of the optical-fiber probe, the vibration motor or the actuator in another component of the shape-sensing system configured to transfer vibrations to the optical-fiber probe through the probe-side connector of the optical-fiber probe.

17. The shape-sensing system of claim 16, wherein the vibration motor or the actuator is started by a switch of another component of the shape-sensing system, speech-recognition logic in another component of the shape-sensing system, or torsion-detection logic in another component of the shape-sensing system.

18. The shape-sensing system of claim 16, wherein each fiber core of the one or more fiber cores of the optical-fiber probe include a number of fiber Bragg grating ("FBG") sensors along at least a distal portion of the optical-fiber probe.

19. The shape-sensing system of claim 18, further comprising:

an optical interrogator configured to send input optical signals into the optical-fiber probe and receive FBG sensor-reflected optical signals from the optical-fiber probe; and a console including one or more processors, memory, and executable instructions stored in the memory that cause the console to perform a set of operations upon execution of the executable instructions by the one or more processors, the set of operations including:

receiving the FBG sensor-reflected optical signals from the optical interrogator;

converting the FBG sensor-reflected optical signals into converted electrical signals with optical signal-converter logic of the console; and determining, in a real-time determination, at least a shape of the optical-fiber probe from the converted electrical signals with shape-sensing logic of the console.

20. The shape-sensing system of claim 19, wherein the set of operations further includes:

tracking vibrating of the optical-fiber probe by the vibration-assisted torsion-management means with vibration-tracking logic of the console; and removing from the converted electrical signals any portion thereof related to vibration-assisted torsion management for at least the shape of the optical-fiber probe.

* * * * *